United States Patent
Itoh et al.

(10) Patent No.: US 6,555,652 B1
(45) Date of Patent: Apr. 29, 2003

(54) TUMOR ANTIGEN PEPTIDE DERIVATIVES

(75) Inventors: Kyogo Itoh, Saga (JP); Shigeki Shichijo, Kurume (JP); Yasuhisa Imai, Kurume (JP)

(73) Assignee: Kyogo Itoh, Saga-ken (JP)

( * ) Notice: Subject to any disclaimer, the term of this patent is extended or adjusted under 35 U.S.C. 154(b) by 0 days.

(21) Appl. No.: 09/555,790

(22) PCT Filed: Dec. 2, 1998

(86) PCT No.: PCT/JP98/05430

§ 371 (c)(1),
(2), (4) Date: Jul. 12, 2000

(87) PCT Pub. No.: WO99/29715

PCT Pub. Date: Jun. 17, 1999

(30) Foreign Application Priority Data

Dec. 5, 1997 (JP) ............................................. 9-335745

(51) Int. Cl.[7] ................................................ C07K 7/06
(52) U.S. Cl. ....................... 530/328; 530/300; 530/350; 514/15
(58) Field of Search ................................ 530/300, 350, 530/328; 514/15

(56) References Cited

FOREIGN PATENT DOCUMENTS

| | | |
|---|---|---|
| EP | 0911397 A1 | 4/1999 |
| EP | 1 041 146 A1 | 10/2000 |
| WO | WO 94/03205 A1 | 2/1994 |
| WO | 9746676 | 12/1997 |

OTHER PUBLICATIONS

Nakao et al., Cancer Research, vol. 55, 4248–4252, Oct. 1, 1995.
Yamazaki, Clinical Immunology, vol. 27, No. 9, Sep. 1995.
Shichijo et al., J. Exp. Med., vol. 187, No. 3, Feb. 2, 1998.
Science, vol. 254: 1643–1647 (1991).
T. Boon et al., J. Exp. Med., vol. 183: 725–729 (1996).
Proc. Nat. Acad. Sci. USA, vol. 91: 3515–3519 (1994).
J. Exp. Med., vol. 176:1453–1457 (1992).
Immunogenetics, vol. 41: 178–228 (1995).
Eur. J. Immunol., vol. 24: 759–764 (1994).
J. Exp. Med., vol. 180: 347–352 (1994).
Int. J. Cancer, vol. 58: 317–323 (1994).
R. T. Kubo et al., J. Immunol., vol. 152: 3913 (1994).
J. Immunol., vol. 155: 4307–4312 (1994).
Cancer Immunol. Immunother., vol. 46: 82–87 (1998).
J. Exp. Med., vol. 185: 453–459 (1997).
J. Immunol., vol. 152: 3904–3912 (1994).
Proc. Natl. Acad. Sci. USA, vol. 91: 6458–6462 (1994).
Gura, T, 1997, Systems for identifying drugs are often faulty, Science, vol. 278, pp. 1041–1042.*
Jain, RK, 1994, Barriers to drug delivery in solid tumors, Scientific American, vol. 271, pp. 58–65.*
Curti, BD, 1993, Physical barriers to drug delivery in tumors, Critical Reviews in Hematology/Oncology, vol. 14, pp. 29–39.*
Bodey, B, et al, 2000, Failure of cancer vaccines: the significant limitations of this approach to immunotherapy, Anticancer Research, vol. 20, pp. 2665–2676.*
Lee, K–H, et al, 1999, Increased vaccine–specific T cell frequency after peptide–based vaccination correlates with increased susceptibility to in vitro stimulation but does not lead to tumor regression, Journal of Immunology, vol. 163, pp. 6292–6300.*
Zaks, TZ, et al, 1998, Immunization with a peptide epitope (p369–377) from HER–2/neu leads to peptide–specific cytotoxic T lymphocytes that fail to recognize HER–2/neu + tumors, Cancer Research, vol. 58, pp. 4902–4908.*
Bergers, G, et al, 2000, Extrinsic regulators of epithelial tumor progression: metalloproteinases, Current Opinion in Genetics & Development, vol. 10, pp. 120–127.*
Ezzell, C, 1995, Cancer "vaccines": an idea whose time has come?, Journal of NIH Research, vol. 7, pp. 46–49.*
Boon, T, 1992, Toward a genetic analysis of tumor ejection antigens, Advances in Cancer Research, vol. 58, pp. 177–210.*
Splitler, Le, 1995, Cancer vaccines: the interferon analogy, Cancer Biotherapy, vol. 10, No. 1, pp. 1–3.*
Timmerman, JM, et al, 1999, Dendritic cell vaccines for cancer immunotherapy, Annual Review of Medicine, vol. 50, pp. 507–529.*
Ikeda et al., Immunity, vol. 6, 199–208, Feb. 1997.
Robbins et al., Journal of Immunology, vol. 154, No. 11, pp. 5944–5950, 1995.
N. Morioka et al., Molecular Immunology, vol. 32, No. 8, ppp. 573–581, 1995.

* cited by examiner

Primary Examiner—Anthony C. Caputa
Assistant Examiner—Stephen L. Rawlings
(74) Attorney, Agent, or Firm—Birch, Stewart, Kolasch & Birch, LLP

(57) ABSTRACT

Tumor antigen peptide derivatives which comprise all or part of an amino acid sequence derived from the amino acid sequence shown in SEQ ID NO: 3 through the alteration of one to several amino acid residues, which are capable of binding to HLA-A24 antigen and thus being recognized by cytotoxic T cells; the use of these tumor antigen peptide derivatives in treating, preventing and diagnosing tumors; and remedies or preventives for tumors containing these peptide derivatives as an active ingredient.

7 Claims, 2 Drawing Sheets

```
                         SEQUENCE LISTING

<160> NUMBER OF SEQ ID NOS: 9

<210> SEQ ID NO 1
    <211> LENGTH: 2527
    <212> TYPE: DNA
    <213> ORGANISM: Homo sapiens
    <220> FEATURE:
    <221> NAME/KEY: CDS
    <222> LOCATION: (39)..(2438)
    <220> FEATURE:
    <221> NAME/KEY: 3'UTR
    <222> LOCATION: (2439)..(2506)
    <220> FEATURE:
    <221> NAME/KEY: 5'UTR
    <222> LOCATION: (1)..(38)

<400> SEQUENCE: 1
ggttcggcgg cagccgggct cggagtggac gtgccact atg ggg tcg tcc aag aag       56
                                             Met Gly Ser Ser Lys Lys
                                              1               5 cat cgc gga gag aag gag gcg gcc ggg acg acg gcg gcg gcc ggc acc       104
    His Arg Gly Glu Lys Glu Ala Ala Gly Thr Thr Ala Ala Ala Gly Thr
                 10                  15                  20 ggg ggt gcc acc gag cag ccg ccg cgg cac cgg gaa cac aaa aaa cac       152
    Gly Gly Ala Thr Glu Gln Pro Pro Arg His Arg Glu His Lys Lys His
             25                  30                  35 aag cac cgg agt ggc ggc agt ggc ggt agc ggt ggc gaa cga cgg aag       200
    Lys His Arg Ser Gly Gly Ser Gly Gly Ser Gly Gly Glu Arg Arg Lys
         40                  45                  50 cgg agc cgg gaa cgt ggg ggc gag cgc ggg agc ggg cgg cgc ggg gcc       248
    Arg Ser Arg Glu Arg Gly Gly Glu Arg Gly Ser Gly Arg Arg Gly Ala
    55                  60                  65                  70 gaa gct gag gcc cgg agc agc acg cac ggg cgg gag cgc agc cag gca       296
    Glu Ala Glu Ala Arg Ser Ser Thr His Gly Arg Glu Arg Ser Gln Ala
                     75                  80                  85 gag ccc tcc gag cgg cgc gtg aag cgg gag aag cgc gat gac ggc tac       344
    Glu Pro Ser Glu Arg Arg Val Lys Arg Glu Lys Arg Asp Asp Gly Tyr
                 90                  95                 100 gag gcc gct gcc agc tcc aaa act agc tca ggc gat gcc tcc tca ctc       392
    Glu Ala Ala Ala Ser Ser Lys Thr Ser Ser Gly Asp Ala Ser Ser Leu
                105                 110                 115 agc atc gag gag act aac aaa ctc cgg gca aag ttg ggg ctg aaa ccc       440
    Ser Ile Glu Glu Thr Asn Lys Leu Arg Ala Lys Leu Gly Leu Lys Pro
             120                 125                 130 ttg gag gtt aat gcc atc aag aag gag gcg ggc acc aag gag gag ccc       488
    Leu Glu Val Asn Ala Ile Lys Lys Glu Ala Gly Thr Lys Glu Glu Pro
    135                 140                 145                 150 gtg aca gct gat gtc atc aac cct atg gcc ttg cga cag cga gag gag       536
    Val Thr Ala Asp Val Ile Asn Pro Met Ala Leu Arg Gln Arg Glu Glu
                    155                 160                 165 ctg cgg gag aag ctg gcg gct gcc aag gag aag cgc ctg aac caa           584
    Leu Arg Glu Lys Leu Ala Ala Ala Lys Glu Lys Arg Leu Leu Asn Gln
                170                 175                 180
```

| | |
|---|---|
| aag ctg ggg aag ata aag acc cta gga gag gat gac ccc tgg ctg gac<br>Lys Leu Gly Lys Ile Lys Thr Leu Gly Glu Asp Asp Pro Trp Leu Asp<br>185 190 195 | 632 |
| gac act gca gcc tgg atc gag agg agc cgg cag ctg cag aag gag aag<br>Asp Thr Ala Ala Trp Ile Glu Arg Ser Arg Gln Leu Gln Lys Glu Lys<br>200 205 210 | 680 |
| gac ctg gca gag aag agg gcc aag tta ctg gag gag atg gac caa gag<br>Asp Leu Ala Glu Lys Arg Ala Lys Leu Leu Glu Glu Met Asp Gln Glu<br>215 220 225 230 | 728 |
| ttt ggt gtc agc act ctg gtg gag gag gag ttc ggg cag agg cgg cag<br>Phe Gly Val Ser Thr Leu Val Glu Glu Glu Phe Gly Gln Arg Arg Gln<br>235 240 245 | 776 |
| gac ctg tac agt gcc cgg gac ctg cag ggc ctc acc gtg gag cat gcc<br>Asp Leu Tyr Ser Ala Arg Asp Leu Gln Gly Leu Thr Val Glu His Ala<br>250 255 260 | 824 |
| att gat tcc ttc cga gaa ggg gag aca atg att ctt acc ctc aag gac<br>Ile Asp Ser Phe Arg Glu Gly Glu Thr Met Ile Leu Thr Leu Lys Asp<br>265 270 275 | 872 |
| aaa ggc gtg ctg cag gag gag gag gac gtg ctg gtg aac gtg aac ctg<br>Lys Gly Val Leu Gln Glu Glu Glu Asp Val Leu Val Asn Val Asn Leu<br>280 285 290 | 920 |
| gtg gat aag gag cgg gca gag aaa aat gtg gag ctg cgg aag aag aag<br>Val Asp Lys Glu Arg Ala Glu Lys Asn Val Glu Leu Arg Lys Lys Lys<br>295 300 305 310 | 968 |
| cct gac tac ctg ccc tat gcc gag gac gag agc gtg gac gac ctg gcg<br>Pro Asp Tyr Leu Pro Tyr Ala Glu Asp Glu Ser Val Asp Asp Leu Ala<br>315 320 325 | 1016 |
| cag caa aaa cct cgc tct atc ctg tcc aag tat gac gaa gag ctt gaa<br>Gln Gln Lys Pro Arg Ser Ile Leu Ser Lys Tyr Asp Glu Glu Leu Glu<br>330 335 340 | 1064 |
| ggg gag cgg cca cat tcc ttc cgc ttg gag cag ggc ggc acg gct gat<br>Gly Glu Arg Pro His Ser Phe Arg Leu Glu Gln Gly Gly Thr Ala Asp<br>345 350 355 | 1112 |
| ggc ctg cgg gag cgg gag ctg gag gag atc cgg gcc aag ctg cgg ctg<br>Gly Leu Arg Glu Arg Glu Leu Glu Glu Ile Arg Ala Lys Leu Arg Leu<br>360 365 370 | 1160 |
| cag gct cag tcc ctg agc aca gtg ggg ccc cgg ctg gcc tcc gaa tac<br>Gln Ala Gln Ser Leu Ser Thr Val Gly Pro Arg Leu Ala Ser Glu Tyr<br>375 380 385 390 | 1208 |
| ctc acg cct gag gag atg gtg acc ttt aaa aag acc aag cgg agg gtg<br>Leu Thr Pro Glu Glu Met Val Thr Phe Lys Lys Thr Lys Arg Arg Val<br>395 400 405 | 1256 |
| aag aaa atc cgc aag aag gag aag gag gta gta gtg cgg gca gat gac<br>Lys Lys Ile Arg Lys Lys Glu Lys Glu Val Val Val Arg Ala Asp Asp<br>410 415 420 | 1304 |
| ttg ctg cct ctc ggg gac cag act cag gat ggg gac ttt ggt tcc aga<br>Leu Leu Pro Leu Gly Asp Gln Thr Gln Asp Gly Asp Phe Gly Ser Arg<br>425 430 435 | 1352 |
| ctg cgg gga cgg ggt cgc cgc cga gtg tcc gaa gtg gag gag gag aag<br>Leu Arg Gly Arg Gly Arg Arg Arg Val Ser Glu Val Glu Glu Glu Lys<br>440 445 450 | 1400 |
| gag cct gtg cct cag ccc ccg tcg gac gac acc cga gtg gag aac<br>Glu Pro Val Pro Gln Pro Pro Ser Asp Asp Thr Arg Val Glu Asn<br>455 460 465 470 | 1448 |
| atg gac atc agt gat gag gag gaa ggt gga gct cca ccg ccg ggg tcc<br>Met Asp Ile Ser Asp Glu Glu Glu Gly Gly Ala Pro Pro Pro Gly Ser<br>475 480 485 | 1496 |
| ccg cag gtg ctg gag gag gac gag gcg gag ctg gag ctg cag aag cag<br>Pro Gln Val Leu Glu Glu Asp Glu Ala Glu Leu Glu Leu Gln Lys Gln<br>490 495 500 | 1544 |

```
ctg gag aag gga cgc cgg ctg cga cag tta cag cag cta cag cag ctg        1592
Leu Glu Lys Gly Arg Arg Leu Arg Gln Leu Gln Gln Leu Gln Gln Leu
        505                 510                 515 cga gac agt ggc gag aag gtg gtg gag att gtg aag aag ctg gag tct        1640
Arg Asp Ser Gly Glu Lys Val Val Glu Ile Val Lys Lys Leu Glu Ser
520                 525                 530 cgc cag cgg ggc tgg gag gag gat gag gat ccc gag cgg aag ggg gcc        1688
Arg Gln Arg Gly Trp Glu Glu Asp Glu Asp Pro Glu Arg Lys Gly Ala
535                 540                 545                 550 atc gtg ttc aac gcc acg tcc gag ttc tgc cgc acc ttg ggg gag atc        1736
Ile Val Phe Asn Ala Thr Ser Glu Phe Cys Arg Thr Leu Gly Glu Ile
                555                 560                 565 ccc acc tac ggg ctg gct ggc aat cgc gag gag cag gag gag ctc atg        1784
Pro Thr Tyr Gly Leu Ala Gly Asn Arg Glu Glu Gln Glu Glu Leu Met
            570                 575                 580 gac ttt gaa cgg gat gag gag cgc tca gcc aac ggt ggc tcc gaa tct        1832
Asp Phe Glu Arg Asp Glu Glu Arg Ser Ala Asn Gly Gly Ser Glu Ser
        585                 590                 595 gac ggg gag gag aac atc ggc tgg agc acg gtg aac ctg gac gag gag        1880
Asp Gly Glu Glu Asn Ile Gly Trp Ser Thr Val Asn Leu Asp Glu Glu
600                 605                 610 aag cag cag cag gat ttc tct gct tcc tcc acc acc atc ctg gac gag        1928
Lys Gln Gln Gln Asp Phe Ser Ala Ser Ser Thr Thr Ile Leu Asp Glu
615                 620                 625                 630 gaa ccg atc gtg aat agg ggg ctg gca gct gcc ctg ctc ctg tgt cag        1976
Glu Pro Ile Val Asn Arg Gly Leu Ala Ala Ala Leu Leu Leu Cys Gln
                635                 640                 645 aac aaa ggg ctg ctg gag acc aca gtg cag aag gtg gcc cgg gtg aag        2024
Asn Lys Gly Leu Leu Glu Thr Thr Val Gln Lys Val Ala Arg Val Lys
            650                 655                 660 gcc ccc aac aag tcg ctg ccc tca gcc gtg tac tgc atc gag gat aag        2072
Ala Pro Asn Lys Ser Leu Pro Ser Ala Val Tyr Cys Ile Glu Asp Lys
        665                 670                 675 atg gcc atc gat gac aag tac agc cgg agg gag gaa tac cga ggc ttc        2120
Met Ala Ile Asp Asp Lys Tyr Ser Arg Arg Glu Glu Tyr Arg Gly Phe
680                 685                 690 aca cag gac ttc aag gag aag gac ggc tac aaa ccc gac gtt aag atc        2168
Thr Gln Asp Phe Lys Glu Lys Asp Gly Tyr Lys Pro Asp Val Lys Ile
695                 700                 705                 710 gaa tac gtg gat gag acg ggc cgg aaa ctc aca ccc aag gag gct ttc        2216
Glu Tyr Val Asp Glu Thr Gly Arg Lys Leu Thr Pro Lys Glu Ala Phe
                715                 720                 725 cgg cag ctg tcg cac cgc ttc cat ggc aag ggc tca ggc aag atg aag        2264
Arg Gln Leu Ser His Arg Phe His Gly Lys Gly Ser Gly Lys Met Lys
            730                 735                 740 aca gag cgg cgg atg aag aag ctg gac gag gag gcg ctc ctg aag aag        2312
Thr Glu Arg Arg Met Lys Lys Leu Asp Glu Glu Ala Leu Leu Lys Lys
        745                 750                 755 atg agc tcc agc gac acg ccc ctg ggc acc gtg gcc ctg ctc cag gag        2360
Met Ser Ser Ser Asp Thr Pro Leu Gly Thr Val Ala Leu Leu Gln Glu
760                 765                 770 aag cag aag gct cag aag acc ccc tac atc gtg ctc agc ggc agc ggc        2408
Lys Gln Lys Ala Gln Lys Thr Pro Tyr Ile Val Leu Ser Gly Ser Gly
775                 780                 785                 790 aag agc atg aac gcg aac acc atc acc aag tgacagcgcc ctcccgtagt          2458
Lys Ser Met Asn Ala Asn Thr Ile Thr Lys
                795                 800 cggccctgcc tcaaccttca tattaaataa agctccctcc ttattttaa aaaaaaaaa        2518
```

-continued aaaaaaaaa                                                                                     2527

<210> SEQ ID NO 2
<211> LENGTH: 800
<212> TYPE: PRT
<213> ORGANISM: Homo sapiens

<400> SEQUENCE: 2

Met Gly Ser Ser Lys Lys His Arg Gly Glu Lys Glu Ala Ala Gly Thr
1               5                   10                  15

Thr Ala Ala Gly Thr Gly Gly Ala Thr Glu Gln Pro Pro Arg His
            20                  25                  30

Arg Glu His Lys Lys His Lys His Arg Ser Gly Gly Ser Gly Gly Ser
            35                  40                  45

Gly Gly Glu Arg Arg Lys Arg Ser Arg Glu Arg Gly Gly Glu Arg Gly
        50                  55                  60

Ser Gly Arg Arg Gly Ala Glu Ala Glu Ala Arg Ser Ser Thr His Gly
65                  70                  75                  80

Arg Glu Arg Ser Gln Ala Glu Pro Ser Glu Arg Val Lys Arg Glu
            85                  90                  95

Lys Arg Asp Asp Gly Tyr Glu Ala Ala Ala Ser Ser Lys Thr Ser Ser
            100                 105                 110

Gly Asp Ala Ser Ser Leu Ser Ile Glu Glu Thr Asn Lys Leu Arg Ala
        115                 120                 125

Lys Leu Gly Leu Lys Pro Leu Glu Val Asn Ala Ile Lys Lys Glu Ala
        130                 135                 140

Gly Thr Lys Glu Glu Pro Val Thr Ala Asp Val Ile Asn Pro Met Ala
145                 150                 155                 160

Leu Arg Gln Arg Glu Glu Leu Arg Glu Lys Leu Ala Ala Lys Glu
            165                 170                 175

Lys Arg Leu Leu Asn Gln Lys Leu Gly Lys Ile Lys Thr Leu Gly Glu
            180                 185                 190

Asp Asp Pro Trp Leu Asp Asp Thr Ala Ala Trp Ile Glu Arg Ser Arg
            195                 200                 205

Gln Leu Gln Lys Glu Lys Asp Leu Ala Glu Lys Arg Ala Lys Leu Leu
        210                 215                 220

Glu Glu Met Asp Gln Glu Phe Gly Val Ser Thr Leu Val Glu Glu Glu
225                 230                 235                 240

Phe Gly Gln Arg Arg Gln Asp Leu Tyr Ser Ala Arg Asp Leu Gln Gly
            245                 250                 255

Leu Thr Val Glu His Ala Ile Asp Ser Phe Arg Glu Gly Glu Thr Met
            260                 265                 270

Ile Leu Thr Leu Lys Asp Lys Gly Val Leu Gln Glu Glu Asp Val
            275                 280                 285

Leu Val Asn Val Asn Leu Val Asp Lys Glu Arg Ala Glu Lys Asn Val
        290                 295                 300

Glu Leu Arg Lys Lys Pro Asp Tyr Leu Pro Tyr Ala Glu Asp Glu
305                 310                 315                 320

Ser Val Asp Asp Leu Ala Gln Gln Lys Pro Arg Ser Ile Leu Ser Lys
            325                 330                 335

Tyr Asp Glu Glu Leu Glu Gly Glu Arg Pro His Ser Phe Arg Leu Glu
            340                 345                 350

Gln Gly Gly Thr Ala Asp Gly Leu Arg Glu Arg Glu Leu Glu Glu Ile
        355                 360                 365

-continued

```
Arg Ala Lys Leu Arg Leu Gln Ala Gln Ser Leu Ser Thr Val Gly Pro
    370                 375                 380

Arg Leu Ala Ser Glu Tyr Leu Thr Pro Glu Met Val Thr Phe Lys
385                 390                 395                 400

Lys Thr Lys Arg Arg Val Lys Lys Ile Arg Lys Glu Lys Glu Val
                405                 410                 415

Val Val Arg Ala Asp Asp Leu Leu Pro Leu Gly Asp Gln Thr Gln Asp
            420                 425                 430

Gly Asp Phe Gly Ser Arg Leu Arg Gly Arg Gly Arg Arg Val Ser
        435                 440                 445

Glu Val Glu Glu Glu Lys Glu Pro Val Pro Gln Pro Leu Pro Ser Asp
    450                 455                 460

Asp Thr Arg Val Glu Asn Met Asp Ile Ser Glu Glu Glu Gly Gly
465                 470                 475                 480

Ala Pro Pro Gly Ser Pro Gln Val Leu Glu Glu Asp Glu Ala Glu
                485                 490                 495

Leu Glu Leu Gln Lys Gln Leu Glu Lys Gly Arg Arg Leu Arg Gln Leu
            500                 505                 510

Gln Gln Leu Gln Gln Leu Arg Asp Ser Gly Glu Lys Val Val Glu Ile
        515                 520                 525

Val Lys Lys Leu Glu Ser Arg Gln Arg Gly Trp Glu Glu Asp Glu Asp
    530                 535                 540

Pro Glu Arg Lys Gly Ala Ile Val Phe Asn Ala Thr Ser Glu Phe Cys
545                 550                 555                 560

Arg Thr Leu Gly Glu Ile Pro Thr Tyr Gly Leu Ala Gly Asn Arg Glu
                565                 570                 575

Glu Gln Glu Glu Leu Met Asp Phe Glu Arg Asp Glu Glu Arg Ser Ala
            580                 585                 590

Asn Gly Gly Ser Glu Ser Asp Gly Glu Glu Asn Ile Gly Trp Ser Thr
        595                 600                 605

Val Asn Leu Asp Glu Glu Lys Gln Gln Gln Asp Phe Ser Ala Ser Ser
    610                 615                 620

Thr Thr Ile Leu Asp Glu Glu Pro Ile Val Asn Arg Gly Leu Ala Ala
625                 630                 635                 640

Ala Leu Leu Leu Cys Gln Asn Lys Gly Leu Leu Glu Thr Thr Val Gln
                645                 650                 655

Lys Val Ala Arg Val Lys Ala Pro Asn Lys Ser Leu Pro Ser Ala Val
            660                 665                 670

Tyr Cys Ile Glu Asp Lys Met Ala Ile Asp Asp Lys Tyr Ser Arg Arg
        675                 680                 685

Glu Glu Tyr Arg Gly Phe Thr Gln Asp Phe Lys Glu Lys Asp Gly Tyr
    690                 695                 700

Lys Pro Asp Val Lys Ile Glu Tyr Val Asp Glu Thr Gly Arg Lys Leu
705                 710                 715                 720

Thr Pro Lys Glu Ala Phe Arg Gln Leu Ser His Arg Phe His Gly Lys
                725                 730                 735

Gly Ser Gly Lys Met Lys Thr Glu Arg Arg Met Lys Lys Leu Asp Glu
            740                 745                 750

Glu Ala Leu Leu Lys Lys Met Ser Ser Ser Asp Thr Pro Leu Gly Thr
        755                 760                 765

Val Ala Leu Leu Gln Glu Lys Gln Lys Ala Gln Lys Thr Pro Tyr Ile
    770                 775                 780

Val Leu Ser Gly Ser Gly Lys Ser Met Asn Ala Asn Thr Ile Thr Lys
```

```
<210> SEQ ID NO 3
<211> LENGTH: 9
<212> TYPE: PRT
<213> ORGANISM: Homo sapiens

<400> SEQUENCE: 3

Glu Tyr Arg Gly Phe Thr Gln Asp Phe
1               5

<210> SEQ ID NO 4
<211> LENGTH: 9
<212> TYPE: PRT
<213> ORGANISM: Artificial Sequence
<220> FEATURE:
<223> OTHER INFORMATION: Variant of (SEQ ID NO 3) derived from Homo
      sapiens
<220> FEATURE:
<221> NAME/KEY: misc_feature
<222> LOCATION: (2)..(2)
<223> OTHER INFORMATION: Xaa can equal Phe, Tyr, Met, or Trp
<220> FEATURE:
<221> NAME/KEY: misc_feature
<222> LOCATION: (9)..(9)
<223> OTHER INFORMATION: Xaa can equal Phe, Leu, Ile, Trp, or Met

<400> SEQUENCE: 4

Glu Xaa Arg Gly Phe Thr Gln Asp Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: Variant of (SEQ ID NO 3) derived from Homo
      sapiens

<400> SEQUENCE: 5

Glu Tyr Arg Gly Phe Thr Gln Asp Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Variant of (SEQ ID NO 3) derived from Homo
      sapiens

<400> SEQUENCE: 6

Glu Tyr Arg Gly Phe Thr Gln Asp Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Variant of (SEQ ID NO 3) derived from Homo
      sapiens

<400> SEQUENCE: 7

Glu Tyr Arg Gly Phe Thr Gln Asp Trp
1               5

<210> SEQ ID NO 8
```

```
-continued

<211> LENGTH: 9
<212> TYPE: PRT
<213> ORGANISM: Artificial Sequence
<220> FEATURE:
<223> OTHER INFORMATION: Variant of (SEQ ID NO 3) derived from Homo
      sapiens

<400> SEQUENCE: 8

Glu Phe Arg Gly Phe Thr Gln Asp Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Variant of (SEQ ID NO 3) derived from Homo
      sapiens

<400> SEQUENCE: 9

Glu Phe Arg Gly Phe Thr Gln Asp Trp
1               5
```

TUMOR ANTIGEN PEPTIDE DERIVATIVES

This application is the national phase under 35 U.S.C. §371 of PCT International Application No. PCT/JP98/05430 which has an International filing date of Dec. 2, 1998, which designated the United States of America.

TECHNICAL FIELD

The present invention relates to novel tumor antigen peptide derivatives.

BACKGROUND ART

It is known that the immune system, particularly T cells, plays an important role in vivo in tumor rejection. Indeed, infiltration of lymphocytes having cytotoxic effects on tumor cells has been observed in human tumor foci (*Arch. Surg.*, 126:200–205, 1990), and cytotoxic T lymphocytes (CTLs) recognizing autologous tumor cells have been isolated from melanomas without great difficulties (e.g., *Immunol. Today*, 8:385, 1987; *J. Immunol.*, 138:989, 1987; and *Int. J. Cancer*, 52:52–59, 1992). In addition, the results of clinical treatment of melanomas by T cell introduction also suggest the importance of T cells in tumor rejection (*J. Natl. Cancer. Inst.*, 86:1159, 1994).

Although it has long been unknown about target molecules for CTLs attacking autologous tumor cells, the recent advance in immunology and molecular biology has gradually revealed such target molecules. Specifically, it has been found that using T cell receptors (TCRs), CTL recognizes a complex between a peptide, called tumor antigen peptide, and a major histocompatibility complex class I antigen (MHC class I antigen, and in the case of human, referred to as HLA antigen), and thereby attacks autologous tumor cells.

Tumor antigen peptides are generated from proteins specific for tumors, that is, tumor antigen proteins. Thus, the proteins are intracellularly synthesized and then degraded in cytoplasm into the peptides by proteasome. On the other hand, MHC class I antigens (HLA antigens) formed at endoplasmic reticulum, when bind to the above tumor antigen peptides, are transported via cis Golgi to trans Golgi, i.e., the mature side and carried to the cell surface where they are presented as an antigen. A tumor-specific CTL recognizes this complex presented as an antigen, and exhibits its anti-tumor effects through the cytotoxic effect or production of lymphokines (*Rinsho-Menneki*, 27(9):1034–1042, 1995). As a consequence of such elucidation of a series of actions, it has become possible to treat tumors by using tumor antigen proteins or tumor antigen peptides as so-called cancer vaccines which enhance tumor-specific CTLs in a patient.

As such tumor antigen proteins, T. Boon et al. identified a protein named MAGE from human melanoma cells for the first time in 1991 (*Science*, 254:1643–1647, 1991), and thereafter several additional tumor antigen proteins have been identified from melanoma cells.

As reviewed by T. Boon et al. (*J. Exp. Med.*, 183, 725–729, 1996), tumor antigen proteins hitherto identified can be divided into the following four categories.

Tumor antigen proteins belonging to the first category are those which are expressed in testis only as normal tissues, while they are expressed in melanoma, head and neck cancer, non-small cell lung cancer, bladder cancer and others, as tumor tissues. Among tumor antigen proteins in this category are the above-described MAGE and analogous proteins constituting a family of more than 12 members (*J. Exp. Med.*, 178:489–495, 1993), as well as BAGE (*Immunity*, 2:167–175, 1995) and GAGE (*J. Exp. Med.*, 182:689–698, 1995), all of which have been identified in melanoma cells.

Although some of such tumor antigen proteins in this category are highly expressed in melanoma, the expression thereof is observed in only 10 to 30% of patients having a particular tumor other than melanoma, and therefore, they cannot be applied widely to treatments or diagnoses of various tumors.

Tumor antigen proteins belonging to the second category are those which are expressed only in melanocytes and retina among normal tissues, and in melanomas among tumor tissues. Since these tissue-specific proteins are highly expressed in melanomas, they would function as tumor antigen proteins specific for melanomas. Among tumor antigen proteins in this category are tyrosinase (*J. Exp. Med.*, 178:489–495, 1993), MART-1 (*Proc. Natl. Acad. Sci. USA*, 91:3515, 1994), gp100 (*J. Exp. Med.*, 179:1005–1009, 1994), and gp75 (*J. Exp. Med.*, 181:799–804, 1995). Genes encoding these proteins have all been cloned from melanoma cells. Melan-A (*J. Exp. Med.*, 180:35, 1994), which has been separately isolated, has proved to be identical with MART-1.

However, the tumor antigen proteins of this category cannot be used widely in the treatments or diagnoses of various tumors, since they are not expressed in tumors other than melanoma.

Tumor antigen proteins belonging to the third category are those which are expressed as tumor antigen peptides recognized by CTL as a result of tumor-specific mutations. Among tumor antigen proteins in this category are mutated CDK4 (*Science*, 269:1281–1284, 1995), β-catenin (*J. Exp. Med.*, 183:1185–1192, 1996), and MUM-1 (*Proc. Natl. Acad. Sci. USA*, 92:7976–7980, 1995). In CDK4 and β-catenin, a single amino acid mutation increases the binding affinity of the peptides to MHC class I antigen, which allows them to be recognized by T cells. In MUM-1, an intron, which normally is not translated, is translated due to mutation, and the resultant peptide is recognized by T cells. However, since such mutations occur at low frequency, they cannot be applied widely to treatments or diagnoses of various tumors.

Tumor antigen proteins belonging to the fourth category are IDS those widely expressed in normal tissues and also recognized by CTL, example of which includes P15 identified from melanoma cells (*J. Immunol.* 154:5944–5955, 1995).

Tumor antigen proteins or peptides hitherto known have been identified in the following manners.

A set of tumor cell and CTL attacking the tumor cell (usually established from lymphocytes of the same patient from whom the tumor cells are obtained) is first provided. Then, the set of cells are used to directly identify tumor antigen peptides, or to determine a gene encoding tumor antigen protein, from which the corresponding tumor antigen peptide is identified.

In the method where tumor antigen peptides are directly identified, tumor antigen peptides bound to MHC class I antigens in tumor cells are extracted under acidic conditions, and separated into various peptides using high-performance liquid chromatography. Tumor antigen peptides are then identified by pulsing cells expressing MHC class I antigen but not expressing tumor antigen protein (for example, B cells from the same patient) with the resultant peptides and examining the reactivity with CTL. The sequences of the peptides thus identified are then determined by, for example, mass spectrometry. In this way, tumor antigen peptides derived from Pmel 17 which is the same molecule as gp100 have been identified from melanoma cells (*Science*, 264:716–719, 1994).

In the method where a gene encoding tumor antigen protein is first obtained which is followed by the identification of the corresponding tumor antigen peptide, such a gene can be cloned using molecular biological techniques. MHC class I antigen gene and cDNAs prepared from tumor cells are co-transfected into cells not expressing tumor antigen proteins (for example, COS cells) for transient expression. The expression products are then repeatedly screened on the basis of their reactivity with CTL to isolate a gene encoding tumor antigen protein. In this way, the genes encoding the above-mentioned MAGE, tyrosinase, MART-1, gp100, and gp75 have been cloned.

The following method can be used to actually deduce and identify a tumor antigen peptide bound to and presented with MHC class I antigen (HLA antigens) on the basis of information about tumor antigen gene. Fragments of various sizes are first prepared from a gene encoding tumor antigen protein by means of PCR, exonucleases, or restriction enzymes, or the like, and cotransfected with MHC class I antigen gene into cells not expressing tumor antigen proteins (e.g., COS cells) for transient expression. The region(s) which include tumor antigen peptides are then identified on the basis of their reactivity with CTL. Subsequently, peptides are synthesized on the basis of the identified regions. Cells expressing MHC class I antigen but not expressing tumor antigen proteins are then pulsed with the synthesized peptides to identify the tumor antigen peptides, for example, by examining their reactions with CTL (*J. Exp. Med.*, 176:1453, 1992; *J. Exp. Med.*, 179:24, 759, 1994). The sequence regularities (motifs) for peptides, which are bound and presented by certain types of MHC such as HLA-A1, -A0201, -A0205, -A11, -A24, -A31, -A6801, -B7, -B8, -B2705, -B37, -Cw0401, and -Cw0602 have been known (*Immunogenetics*, 41:178–228, 1995), and therefore, candidates for tumor antigen peptides may also be designed by making reference to such motifs, synthesized and examined in the same way as described above (*Eur. J. Immunol.*, 24:759, 1994; *J. Exp. Med.*, 180:347, 1994).

According to procedures as described above, various tumor a antigen proteins and tumor antigen peptides have been hitherto identified. As described above, however, some of the known tumor antigen proteins are expressed only in limited tumors, and others are expressed only in a small number of patients having a particular tumor even if they are expressed in various kinds of tumor, and therefore, they cannot be used widely in the treatments or diagnoses of various tumors.

DISCLOSURE OF INVENTION

One of the purposes of the present invention is to provide tumor antigen peptide derivatives which can be used widely and universally without limitations regarding the kind of tumor or the subjects, in particular, tumor antigen proteins, tumor antigen peptides corresponding thereto, and derivatives thereof which can be widely applied to treatments and diagnoses of tumors with high incidence such as squamous cell carcinoma. Thus, it is one of purposes of the present invention to provide novel tumor antigen peptide derivatives derived from a tumor other than melanomas, in particular, from a squamous cell carcinoma, and also methods, compositions, kits, and the like, for treating, preventing or diagnosing tumors by the use of said tumor antigen peptide derivatives. It is also a purpose of the present invention to provide tumor antigen peptide derivatives restricted to HLA-A24, which is an HLA antigen carried by a large part of human subjects.

To this end, the present inventors have established a squamous cell carcinoma cell line KE-4 derived from esophageal cancer (hereinafter referred to as esophageal cancer cell line KE-4 or simply as KE-4), and also established CTL (hereinafter referred to as KE-4CTL) which recognizes tumor antigen peptides restricted to HLA antigens such as HLA-A2601, HLA-A2402, and the like, which are expressed by said KE-4 (*Cancer Res.*, 55:4249–4253, 1995).

Fibroblast cell line VA-13 was then cotransfected with a recombinant plasmid of cDNA library prepared from KE-4 and a recombinant plasmid containing HLA-A2601 cDNA. The screening of a gene(s) encoding novel tumor antigen protein was carried out by treating the resulting transfectants with KE-4CTL, and measuring the amount of produced IFN-γ to determine whether KE-4CTL was activated or not. As a result, the inventors succeeded in cloning a novel gene encoding a novel tumor antigen protein for the first time from tumor cells other than melanomas. The nucleotide sequence of the cloned gene is shown in SEQ ID NO: 1 and the deduced amino acid sequence is shown in SEQ ID NO: 2.

Subsequently, the present inventors tried to identify the portions in the amino acid sequence of the above tumor antigen protein that actually function as tumor antigen peptides, and identified various tumor antigen peptide portions restricted to HLA-A26, HLA-A24, and the like.

Among them, a peptide having the amino acid sequence at positions 690 to 698 (SEQ ID NO: 3) in the amino acid sequence shown in SEQ ID NO: 2 was identified as an HLA-A24-restricted tumor antigen peptide. The present inventors then prepared various peptide derivatives by altering an amino acid residue(s) in the HLA-A24-restricted tumor antigen peptide shown in SEQ ID NO: 3 and determined their activities, which revealed that the derivatives also have the activity as a tumor antigen peptide.

The present invention was completed on the basis of such findings.

Thus, the gist of the present invention is to provide tumor is antigen peptide derivatives which comprise all or part of an amino acid sequence wherein one to several amino acid residues in the amino acid sequence shown in SEQ ID NO: 3 are altered, and which derivatives are capable of binding to HLA-A24 antigen and thus being recognized by cytotoxic T cells.

BRIEF DESCRIPTION OF THE DRAWINGS

In FIG. 1 a), KE-4, KE-3, TE-8, and TE-9 indicate esophageal cancer cell lines; Kuma-1 indicates a head and neck cancer cell line; HSC-4 indicates a mouth cancer cell line; Bec-1 indicates a B cell line; KMG-A indicates a gallbladder cancer cell line; R-27 indicates a breast cancer cell line, KIM-1, KYN-1, and HAK-3 indicate hepatic cancer cell lines; and M36 and M37 indicate melanoma cell lines. From FIG. 1, it can be seen that the mRNA for the tumor antigen protein encoded in the clone 6DI is widely expressed in various cancer cells and normal tissues.

DETAILED DESCRIPTION OF THE PREFERRED EMBODIMENTS

Figure 1:
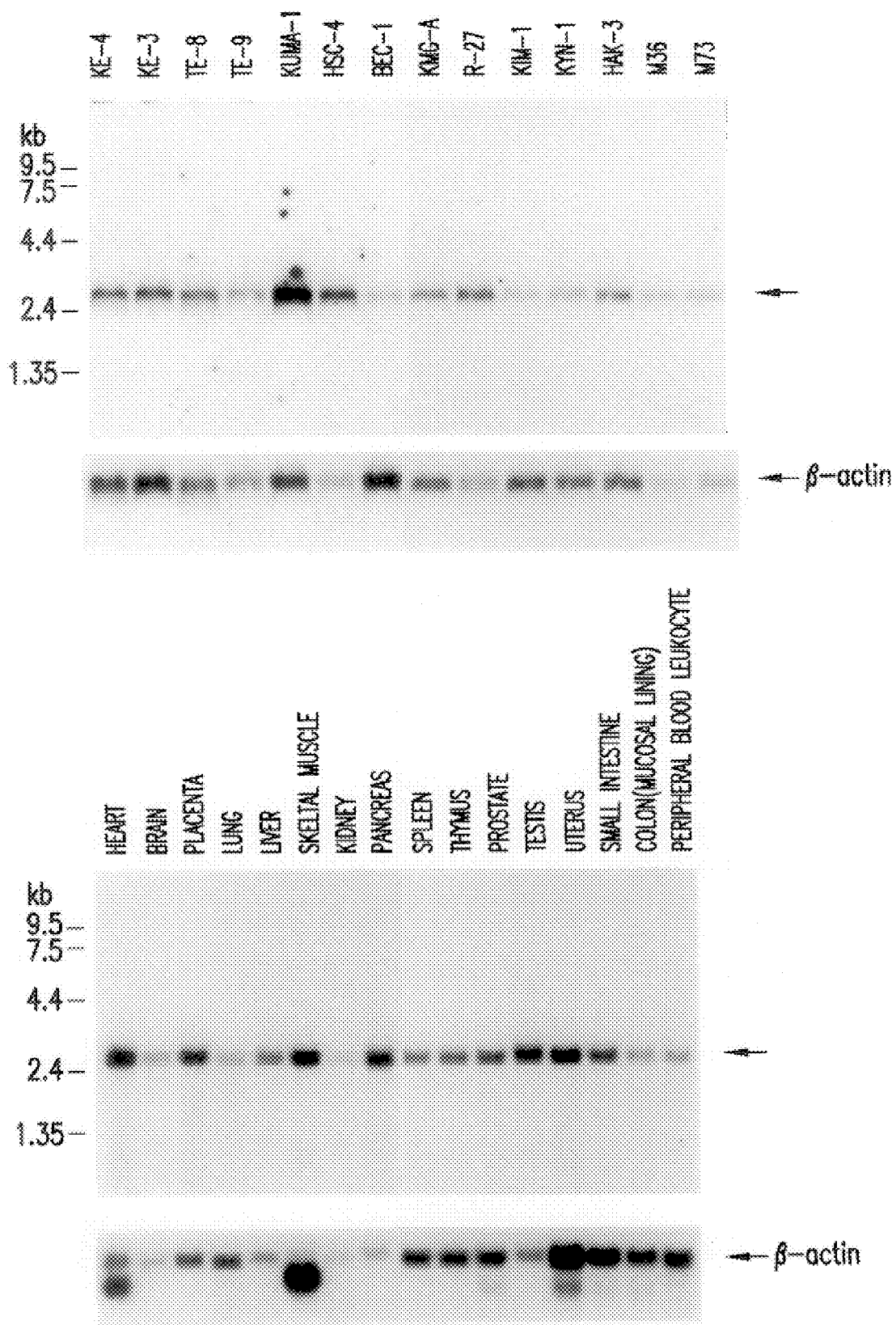
FIG. 1 depicts electrophoretograms showing the result of analysis of distribution of tumor antigen protein mRNA expression in various cell lines (a) and various tissues (b), including heart, brain, placenta, lung, liver, skeletal muscle, kidney, pancreas, spleen, thymus, prostate, testis, uterus, small intestine, and colon (mucosal lining), as well as in peripheral blood leukocyte, by Northern blot hybridization using, as a DNA probe, the inserted sequence portion in a recombinant plasmid 6DI that encodes the tumor antigen protein cloned from the esophageal cancer cell line KE-4.

In this specification, "tumor antigen peptide derivatives" of the present invention refer to those which comprise all or part of an amino acid sequence wherein one or more amino acid residues and preferably one to several amino acid residues in the amino acid sequence shown in SEQ ID NO: 3 are altered, and which have the activity as a tumor antigen peptide, i.e., the ability to bind to HLA-A24 antigen and be recognized by CTL. A peptide having the amino acid sequence of SEQ ID NO: 3 is an HLA-A24 restricted tumor antigen peptide which is located at amino acid No. 690 to 698 of the amino acid sequence of the tumor antigen protein shown in SEQ ID NO: 2.

Accordingly, all the peptides that contain all or part of a derivative wherein one or more amino acid residues in the amino acid sequence of the tumor antigen peptide shown in SEQ ID NO: 3 are altered and have the activity as a tumor antigen peptide, i.e., which peptides are capable of binding to HLA-A24 antigen and thus being recognized by CTL, fall within the scope of tumor antigen peptide derivatives of the present invention.

In the present invention, "capable of binding to HLA-A24 antigen and thus being recognized by CTL" means that the tumor antigen peptide derivative can bind to HLA-A24 antigen to form a complex and that CTL can recognize such complex.

In the present invention, the "alteration" of amino acid residues means substitution, deletion and/or addition of amino acid residues, and a preferred example is substitution of amino acid residues. The following descriptions mainly concern substitution of amino acid residues, but the same descriptions are also applicable to deletion or addition of amino acid residues.

Tumor antigen peptide derivatives of the present invention can be identified, for example, by synthesizing a candidate peptide which comprises all or part of an amino acid sequence wherein one or more, preferably one to several, amino acid residues in the amino acid sequence shown in SEQ ID NO: 3 are substituted with other amino acid residues, and then conducting an assay for determining whether or not the complex between said candidate peptide and HLA-A24 antigen is recognized by CTL.

Although the number and the position of amino acid residues to be substituted may be determined arbitrarily so long as the activity as a tumor antigen peptide is retained, it is preferred that one to several residues are substituted since the peptide fragment shown in SEQ ID NO: 3 consists of nine amino acid residues.

Synthesis of Peptides

Synthesis of peptides may be achieved by the methods usually used in peptide chemistry, for example, those described in the literatures such as "Peptide Synthesis", Interscience, New York, 1966; "The Proteins", vol. 2, Academic Press Inc., New York, 1976; "Pepuchido-Gosei", Maruzen, 1975; "Pepuchido-Gosei-no-Kiso-to-Jikkenn", Maruzen, 1985; and "Iyakuhin-no-Kaihatu, Zoku, vol. 14, Peputido-Gosei", Hirokawa Shoten, 1991.

Recognition by HLA-Antigen-restricted CTL

It can be examined whether or not a synthesized candidate peptide is capable of binding to HLA-A24 antigen and thus being recognized by CTL, for example, by the following methods.

(1) According to the method described in J. Immunol., 154:2257 (1995), peripheral blood lymphocytes are isolated from an HLA-A24 antigen-positive human, and it is determined whether CTL that specifically recognizes HLA-A24-positive cells pulsed with the candidate peptide is induced or not, when the lymphocytes are stimulated in vitro by adding the candidate peptide. The presence or absence of CTL induction may be determined, for example, by measuring the amounts of various cytokines (for example, IFN-γ) produced by CTL in response to the antigen peptide-presenting cells using an enzyme-linked immunosorbent assay (ELISA) or the like. Alternatively, a method in which the cytotoxicity of CTL against antigen peptide-presenting cells labeled with $^{51}Cr$ is measured ($^{51}Cr$ release assay, Int. J. Cancer, 58:317, 1994) may also be used. HLA-A24-positive cells used in the above assays may be generally available cells such as an esophageal cancer cell line KE-4 (FERM BP-5955) or SKG-IIIa cells (JCRB 0232).

(2) Furthermore, the examination can also be done by introducing an HLA-A24 cDNA expressing plasmid into COS-7 cells (ATCC No. CRL1651) or VA-13 cells (RIKEN CELL BANK, The Institute of Physical and Chemical Research), pulsing the obtained cells with the above candidate peptide, reacting them with KE-4CTL (Deposit Number: FERM BP-5954), an HLA-A24-restricted CTL line, and then measuring the amounts of various cytokines (for example, IFN-γ) produced by KE-4CTL (J. Exp. Med., 187:277, 1998).

Illustrative examples of various assay as described above are shown in Reference Examples 7 and 8 as well as Example 2 below.

In addition, the binding affinity of a tumor antigen peptide derivative to HLA-A24 antigen may easily be measured in a cell-free system using a competitive inhibition assay for binding to the HLA antigen between said derivative and the standard peptide (SEQ ID NO: 3) labeled with a radioisotope (R. T. Kubo et at., J. Immunol., 152:3913, 1994).

Length of a tumor antigen peptide derivative of the present invention is not specifically restricted provided that it binds to HLA-A24 antigen and is thus recognized by CTL. According to the purposes of the present invention, tumor antigen peptide derivatives of the present invention include those not only presented by themselves on the surface of antigen-presenting cells after binding to HLA-A24 antigen, but also those fragmented as appropriate within target cells to yield peptide fragments of an appropriate length, which fragments comprise all or part of an amino acid sequence wherein one to several amino acid residues in the amino acid sequence of SEQ ID NO: 3 are altered and are capable of binding to HLA-A24 antigen and thus being recognized by CTL.

Preferably, a peptide fragment that in itself binds to HLA-A24 antigen and is thus presented has a length of 8 to 11 amino acids. Accordingly, examples of peptide derivatives obtainable by amino acid substitution include 1) a peptide consisting of 9 amino acids having an amino acid sequence in which one to several amino acid residues in the amino acid sequence shown in SEQ ID NO: 3 are substituted by other amino acid residue(s); or 2) a peptide of about 10 to 11 amino acids in length that comprises the whole peptide of the above 1) or a peptide consisting of about 8 amino acids that comprises part of the peptide of the above 1), wherein the derivatives retain the tumor antigen peptide activity of binding to HLA-A24 antigen and thus being recognized by CTL.

Intended tumor antigen peptide derivatives can be obtained by synthesizing various peptides in which an amino acid or amino acids at any position(s) in the amino acid sequence of SEQ ID NO. 3 are altered, and screening on the basis of the activity as a tumor antigen peptide according to the descriptions in the present specification.

There are certain rules (motifs) in the sequences of antigen peptides bound and presented by HLA antigen. Concerning the motif for HLA-A24, it is known that in the sequence of peptides consisting of 8 to 11 amino acids, the amino acid at the second position from the N-terminus is phenylalanine, tyrosine, methionine, or tryptophan, and the C-terminal amino acid is phenylalanine, leucine, isoleucine, tryptophan, or methionine (*Immunogenetics*, 41:178–228, 1995; *J. Immunol.*, 152:3913, 1994; *J. Immunol.*, 155:4307, 1994). In addition, derivatives obtainable by substituting an amino acid consistent with such motif with another amino acid having analogous properties may also potentially be accepted as HLA-A24 antigen binding peptide.

Accordingly, examples of tumor antigen peptide derivative of the present invention include a peptide derivative that comprises all or part of an amino acid sequence wherein the amino acid residue(s) at the second position and/or the ninth position (the C-terminus) in the amino acid sequence shown in SEQ ID NO: 3 are substituted by other amino acid residues and that has the activity of binding to HLA-A24 antigen and thus being recognized by CTL.

Thus, the present invention provides a tumor antigen peptide derivative that comprises all or part of an amino acid sequence wherein the amino acid residue(s) at the second position and/or the ninth position in the amino acid sequence shown in SEQ ID NO: 3 are substituted by other amino acid residues and that is capable of binding to HLA-A24 antigen and thus being recognized by CTL.

In preferred peptide derivatives, the amino acid residue(s) at tho second position and/or the ninth position in the amino acid sequence shown in SEQ ID NO: 3 are substituted by an amino acid residue consistent with the above motif. Specifically, preferred tumor antigen peptide derivatives are those comprising all or part of an amino acid sequence wherein tyrosine at the second position in the amino acid sequence shown in SEQ ID NO: 3 is substituted by phenylalanine, methionine, or tryptophan and/or phenylalanine at the ninth position is substituted by leucine, isoleucine, tryptophan, or methionine, and having the activity described above, which amino acid sequence is shown in SEQ ID NO: 4.

Thus, in another embodiment, the present invention provides a tumor antigen peptide derivative comprising all or part of the amino acid sequence shown in SEQ ID NO: 4 and being capable of binding to HLA-A24 antigen and thus being recognized by CTL.

Furthermore, preferred examples of a tumor antigen peptide derivative that contains substitution of amino acid residue according to the above motif are tumor antigen peptide derivatives that comprise all or part of an amino acid sequence wherein phenylalanine at the ninth position in the amino acid sequence shown in SEQ ID NO: 3 is substituted by tryptophan; leucine, or isoleucine; tumor antigen peptide derivatives that comprise all or part of an amino acid sequence wherein tyrosine at the second position in the amino acid sequence shown in SEQ ID NO: 3 is substituted by phenylalanine; and tumor antigen peptide derivatives that contain a combination of such substitutions.

Accordingly, in a preferred embodiment, the present invention provides a tumor antigen peptide derivative comprising all or part of an amino acid sequence wherein phenylalanine at the ninth position in the amino acid sequence shown in SEQ ID NO: 3 is substituted by tryptophan, leucine, or isoleucine and being capable of binding to HLA-A24 antigen and thus being recognized by CTL.

In a further preferred embodiment, the present invention provides a tumor antigen peptide derivative comprising all or part of an amino acid sequence wherein tyrosine at the second position in the amino acid sequence shown in SEQ ID NO: 3 is substituted by phenylalanine and being is capable of binding to HLA-A24 antigen and thus being recognized by CTL.

In a still further preferred embodiment, the present invention provides a tumor antigen peptide derivative comprising all or part of an amino acid sequence wherein phenylalanine at the ninth position in the amino acid sequence shown in SEQ ID NO: 3 is substituted by tryptophan, leucine, or isoleucine, and tyrosine at the second position is also substituted by phenylalanine, and being capable of binding to HLA-A24 antigen and thus being recognized by CTL.

A particularly preferred tumor antigen peptide derivative comprises all or part of the amino acid sequence shown in SEQ ID NO: 5.

Tumor antigen peptide derivatives of the present invention bind to HLA-A24, which is an HLA antigen found in a large part of human subjects (for example, in about 60% of Japanese), and presented thereby. Accordingly, the present derivatives are expected to be useful as novel anti-tumor agents, since they are generally usable in most of tumor patients and also widely applicable to tumors of high incidence such as squamous cell carcinoma. In this connection, squamous cell carcinoma is one of human cancers that are most frequently found, and particularly esophageal cancer and lung cancer are known to be relatively resistant to current chemotherapy or radiotherapy.

As described below in detail, tumor antigen peptide derivatives of the present invention are useful in vivo and in vitro for various purposes including treatment, prophylactic, or diagnosis of tumors.

Thus, the present invention also provides a therapeutic or prophylactic agent for tumors that comprises as an active ingredient at least one of the above-described tumor antigen peptide derivatives of the present invention.

When used with the aim of treating or preventing tumors, at least one of, or a combination of two or more of, tumor antigen peptide derivatives of the present invention is administered to a patient, if necessary, in combination with, for example, other tumor antigen peptides. When a therapeutic or prophylactic agent for tumors of the present invention is administered to a patient who is HLA-A24-positive and is also positive in respect to the tumor antigen protein from which the tumor antigen peptide derivatives of the present invention are derived, the said peptide derivative is presented at high density with HLA-A24 antigen of antigen-presenting cells, then CTL specific for the presented HLA-A24 antigen complex proliferates and destroys tumor cells. As a result, the tumor of the patient may be treated, or proliferation or metastasis of the tumor may be prevented. As described above, the tumor antigen protein from which tumor antigen peptide derivatives of the present invention are derived is widely expressed, for example, on squamous cell carcinomas such as esophageal cancer, lung cancer, and the like. A therapeutic or prophylactic agent for tumors of the present invention has therefore an advantage of having a wide range of application. Furthermore, although the above squamous cell carcinomas often exhibit resistance to chemotherapy and radiotherapy, a combined use of a therapeutic agent for tumors of the present invention make it possible to achieve a desired therapeutic effect. In addition, it is also a great advantage that treatment can be given without specifying the site at which the cancer develops.

A therapeutic or prophylactic agent for tumors containing a tumor antigen peptide derivative of the present invention may be administered along with an adjuvant in order to effectively establish the cellular immunity, or may be administered in a particulate dosage form. For such purpose, those adjuvants described in the literature (*Clin. Microbiol. Rev.*, 7:277–289, 1994) are applicable. In addition, dosage forms which allow the foreign antigen peptide derivatives to be efficiently presented on HLA antigen, such as liposomal preparations, particulate preparations in which the derivatives are bound to beads having a diameter of several μm, or preparations in which the derivatives are attached to lipids, are also used. Administration may be achieved, for example, intradermally, hypodermically, by intravenous injection, or the like. Although the dose of a tumor antigen peptide derivative of the present invention administered may be adjusted as appropriate depending on, for example, the disease to be treated, the age and the body weight of a particular patient, it would be usually from 0.0001 mg to 1000 mg, preferably 0.001 mg to 1000 mg, and more preferably 0.1 mg to 10 mg of the derivative every several days to every several months.

Furthermore, tumor antigen peptide derivatives of the present invention can be used for in vitro induction of antigen-presenting cells and such cells are useful in, for instance, the treatment of tumors.

Accordingly, the present invention provides an antigen-presenting cell which comprises a complex between HLA-A24 antigen and a tumor antigen peptide derivative of the present invention, the complex being presented on the surface of an isolated cell which has an antigen-presenting ability and is derived from a tumor patient.

The present invention further provides a therapeutic agent for tumors which comprises the above antigen-presenting cells as an active VD ingredient.

Although the "cell having an antigen-presenting ability" is not specifically restricted to any cell so long as it is expressing HLA-A24 antigen capable of presenting a tumor antigen peptide derivative of the present invention on the surface, dendritic cells, which is reported to have an especially high antigen-presenting ability, are preferred.

In order to prepare such antigen-presenting cells, cells having an antigen-presenting ability are isolated from a tumor patient, and pulsed ex vivo with a tumor antigen peptide derivative of the present invention to form a complex between HLA-A24 antigen and the peptide derivative (*Cancer Immunol. Immunother.*, 46:82, 1998).

A therapeutic agent for tumors that comprises the above antigen-presenting cells as an active ingredient preferably contains physiological saline, phosphate buffered saline (PBS), culture medium, or the like in order to stably maintain the antigen-presenting cells. Administration may be achieved, for example, intravenously, hypodermically, or intradermally. By returning the above therapeutic agent for tumors into the patient's body, specific CTL is efficiently induced in the patient who is HLA-A24 positive and is also positive for the tumor antigen protein from which tumor antigen peptide derivatives of the present invention are derived. The tumor can be thereby treated, and furthermore its metastasis may also be prevented.

In addition, another example of in vitro use of tumor antigen peptide derivatives of the present invention may be in the following adoptive immunotherapy.

In the case of melanoma, it has been observed that an adoptive immunotherapy wherein intratumoral T cell infiltrate taken from the patient himself/herself are cultured ex vivo in large quantities, and then returned into the patient achieves an therapeutic gain (*J. Natl. Cancer. Inst.*, 86:1159, 1994). Furthermore, in mouse melanoma, suppression of metastasis has been observed by stimulating splenocytes in vitro with a tumor antigen peptide TRP-2, thereby proliferating CTLs specific for the tumor antigen peptide, and then administering said CTLs into a mouse carrying grafted melanoma (*J. Exp. Med.*, 185:453, 1997). This resulted from in vitro proliferation of CTL that specifically recognizes the complex between an HLA antigen of antigen-presenting cells and the tumor antigen peptide. A method for treating tumors which comprises in vitro stimulating peripheral blood lymphocytes from a patient with a tumor antigen peptide derivative of the present invention to proliferate tumor-specific CTLs, and returning the CTLs into the patient is believed to be useful.

Accordingly, the present invention also provides cytotoxic T cells that specifically recognize a complex between HLA-A24 antigen and the above tumor antigen peptide derivative.

Furthermore, the present invention provides a therapeutic agent for tumor which comprises the above cytotoxic T cells as an active ingredient.

It is preferred that the therapeutic agent contains physiological saline, phosphate buffered saline (PBS), culture medium, or the like in order to stably maintain CTLs. Administration may be achieved, for example, intravenously, hypodermically, or intradermally. By returning the above therapeutic agent into the patient's body, the toxic effect of CTLs on tumor cells is enhanced in the patient who is HLA-A24 positive and is also positive for the tumor antigen protein from which tumor antigen peptide derivatives of the present invention are derived. The destruction of tumor cells leads to the treatment of tumor and the prevention of metastasis.

To use a tumor antigen peptide derivative of the present invention in diagnosis of tumors, for example, an antibody against the tumor antigen peptide derivative is prepared in a conventional manner and labeled appropriately, if necessary. The antibody is used to detect the presence of the antigen in a sample (such as blood, a tumor tissue, or the like) obtained from a patient suspected to have a tumor, thereby diagnosing the presence or absence of tumors. A tumor antigen peptide derivative of the present invention itself can also be used as a diagnostic agent for detecting the presence of antibody in the above-mentioned sample such as blood or tumor tissue to diagnose the presence or absence of tumors.

The present invention also provides a method of treating, preventing, or diagnosing tumors using a tumor antigen peptide derivative described above, antigen-presenting cells that are presenting said tumor antigen peptide derivative, cytotoxic T cells that specifically recognize a complex between said tumor antigen peptide derivative and HLA-A24 antigen. Furthermore, tumor antigen peptide derivatives of the present invention are also useful as research reagents.

The following Examples are provided to further illustrate the present invention and are not to be construed as limiting the scope thereof.

REFERENCE EXAMPLE

Cloning of a Tumor Antigen Protein cDNA and Indentification of HLA-A24- and HLA-A26-restricted Tumor Antigen Peptides (1) Establishment of Cytotoxic T Lymphocyte (CTL) Cell Line Against Esophageal Cancer Cell Line According to the disclosure of Nakao et al., Cancer Res., 55:4248–4252 (1995); CTL, against an esophageal cancer cell line, KE-4, belonging to squamous cell carcinomas when classified on the basis of the tissue type was established from peripheral blood monocytes of a patient, named KE-4CTL, and used in experiments. The esophageal cancer cell line KE-4 and KE-4CTL have been deposited at The National Institute of Bioscience and Human Technology (1-1-3 Higashi, Tsukuba, Ibaraki, Japan) under International Deposition Nos. FERM BP-5955 and FERM BP-5954, respectively, both on May 23, 1997. Furthermore, typing of HLA class I molecules of KE-4 was conducted according to the above-noted disclosure of Nakao et al., and it was confirmed that they are HLA-A2402, -A2601, B54, -B60, -Cw1, and -Cw3.

(2) Preparation of HLA-A2661 cDNA and HLA-A2402 cDNA

Using KE-4, a recombinant plasmid was prepared by incorporating cDNA for HLA-A2601 into an expression vector pCR3 (INVITROGEN) according to the disclosure of Nakao et al., Cancer Res., 55:4248–4252 (1995). Another recombinant plasmid for HLA-A2402 was also prepared in the similar manner.

(3) Preparation of cDNA Library Derived from KE-4

Poly (A)⁺ mRNA was prepared from KE-4 by isolation of total RNA fraction and purification on oligo (dT) column using mRNA Purification system (manufactured by Pharmacia Biotech) according to the manufacturer's protocol. cDNAs having Not I adapter and Sca I adapter linked to each terminus were prepared from mRNAs using SuperScript™ Plasmid System (Gibco BRL) according to the manufacturer's protocol, and then ligated to an expression vector, plasmid pSV-SPORT1 (Gibco BRL), digested with restriction enzymes Not I and Sal I, to yield recombinant plasmids. The recombinant plasmids were introduced into *E. coli.* ElectroMAX DH10B/p3™ cells (Gibco BRL) using electric pulses in Gene Pulser (Bio-Rad) under conditions of 25 $\mu$F and 2.5 kV. Transformants into which the recombinant plasmids had been introduced were selected in LB medium (1% bacto-trypton, 0.5% yeast extract, 0.5% NaCl, pH7.3) containing ampicillin (50 $\mu$g/ml).

(4) Screening of Tumor Antigen Protein Gene

The recombinant plasmid DNAs were recovered from pools of about 100 transformants described in the above (3) as follows. A hundred transformants were introduced and cultured in each well of 96-well U-bottomed microplate containing LB medium plus ampicillin (50 $\mu$g/ml). Part of the culture was then transferred to another 96-well U-bottomed microplate containing 0.25 ml per well of TYGPN medium (F. M. Ausubel et al., *Current Protocols in Molecular Biology*, John Wiley & Sons, Inc.), and cultured for 48 hours at 37° C. The remaining cultures in LB medium on the microplate were stored in frozen. Preparation of recombinant plasmid DNAs from transformants cultured in TYGPN medium was achieved in the microplate by alkaline lysis (F. M. Ausubel et al., *Current Protocols in Molecular Biology*, John Wiley & Sons, Inc.). The recombinant plasmid DNAs recovered by isopropanol precipitation were suspended in 50 $\mu$l of 10 mM Tris, 1 mM EDTA, pH 7.4, containing 20 ng/ml RNase.

Fibroblast cell line, VA-13 cells (RIKEN CELL BANK, The Institute of Physical and Chemical Research; *Ann. Med. Exp. Biol. Fenn.*, 44:242–254, 1966) were doubly transfected with the recombinant plasmid for KE-4 cDNA and the recombinant plasmid for HLA-A2601 cDNA using Lipofectin method as follows. Seven thousands VA-13 cells were placed in each well of 96-well flat-bottomed microplate, and incubated for 2 days in 100 $\mu$l of RPMI 1640 medium containing 10% FCS. Using Lipofectin reagent (Gibco BRL), 30 $\mu$l of 70 $\mu$l mixture consisting of 25 $\mu$l of the recombinant plasmid for KE-4 cDNA corresponding to about 100 transformants, 10 $\mu$l (200 ng) of the recombinant plasmid for HLA-A2601 cDNA described in (2) of Reference Example, and 35 $\mu$l of about 35-fold diluted Lipofectin reagent was added to VA-13 cells to be doubly transfected. Transfectants were prepared in duplicate. After 5 hours, 200 $\mu$l of culture medium containing 10% FCS was added to the transfectants, and further incubated for 72 hours at 37° C. After removing the culture medium, 10,000 KE-4CTL cells were added to each well, and cultured for 24 hours at 37° C. in 100 $\mu$l of culture medium containing 10% FCS and 25 U/ml IL-2. The culture medium was recovered, and the amount of IFN-$\gamma$ in the culture supernatant produced by KE-4CTL was measured by ELISA. Specifically, an anti-human IFN-$\gamma$ mouse monoclonal antibody was adsorbed on wells of 96-well microplate as a solid-phased antibody, and after blocking non-specific bindings with bovine serum albumin, allowed to bind with IFN-$\gamma$ in the above-described culture supernatant. Anti-human IFN-$\gamma$ rabbit polyclonal antibody as a detection antibody was then allowed to bind, and after binding with an anti-rabbit immunoglobulin goat antibody labeled with alkaline phosphatase, reacted with para-nitrophenyl phosphate as a chromogenic substrate. After quenching the reaction by adding an equal volume of 1N NaOH, absorbance at 405 nm was measured. The absorbance was compared with that obtained with standard IFN-$\gamma$ to determine the amount of IFN-$\gamma$ in the supernatant.

Regarding four groups in which high production of IFN-$\gamma$ was observed, corresponding frozen-stored pools of about 100 transformants containing recombinant plasmids for KE-4 cDNA were used in the following screening. The pools of the transformants were plated on LB agar medium containing ampicillin (50 $\mu$g/ml) to obtain colonies. Two hundreds colonies for each group (total 800 colonies) were cultured as described above so that a single kind of transformant is included in each well, thereby recombinant plasmid DNAs for KE-4 cDNA were prepared. Then, VA-13 cells were doubly transfected with the recombinant plasmid for KE-4 cDNA and the recombinant plasmid for HLA-A2601 cDNA followed by cocultivation with KE-4CTL, and IFN-$\gamma$ produced due to KE-4CTL reaction was quantitatively determined as described above in order to select positive plasmids. In this manner, a single KE-4 cDNA recombinant plasmid clone was selected and named 6DI. Furthermore, similar procedures were repeated with 6DI to determine the amount of IFN-γ produced by KE-4CTL according to the same method as that described above. The results are shown in the following TABLE 1.

TABLE 1

| Target cell | Amount of IFN-γ produced by KE-4CTL (pg/ml) |
|---|---|
| VA-13 cell | 0 |
| VA-13 cell + HLA-A2601 | 1.8 |
| VA-13 cell + 6DI | 4.3 |
| VA-13 cell + HLA-A2601 + 6DI | 24.0 |
| VA-13 cell + HLA-A0201[1)] | 0.9 |
| VA-13 cell + HLA-A0201 + 6DI[1)] | 3.0 |

[1)]For comparison, HLA of different type was transfected.
(These date was obtained by transfection using the following amounts of DNA: 200 ng of HLA-A2601 or HLA-A0201, 100 ng of 6DI.)

(5) Expression Analysis for Tumor Antigen Protein Gene by Northern Hybridization RNAs were prepared from various cell lines using RNAzol B (TEL-TEST, Inc.). Five µg of RNA was denatured in the presence of formaldehyde and formaldehyde, electrophoresed on agarose, then transferred and fixed onto Hybond-N+ Nylon membrane (Amersham). As RNAs from normal tissues, commercially available membranes (Clontech) onto which mRNAs have been preblotted were used. The inserted sequence region of the recombinant plasmid 6DI cloned in (4) of Reference Example was labeled with $^{32}$P using Multiprime DNA labeling system (Amersham) to prepare DNA probe. According to the known method (Nakayama et at., *Bio-Jikken-Illustrated*, vol. 2, "Idenshi-Kaiseki-No-Kiso (A Basis for Gene Analysis)", pp. 148–151, Shujunsha, 1995), this probe was allowed to hybridize to RNAs on the membranes, and subjected to autoradiography to detect mRNA for tumor antigen protein gene of the present invention. The membranes used for the detection of mRNA for said gene were boiled in 0.5% aqueous sodium dodecyl sulfate to remove the probe, and subjected to Northern hybridization in a similar manner using β-actin as a probe which is constitutively expressed in cells, in order to detect mRNA which was used as an internal standard. The results are shown in FIG. 1. It became apparent from these results that mRNA for tumor antigen protein gene of the present invention is widely expressed in various cancer cells and normal tissues, and is about 2.5 kb in full length (FIG. 1)

(6) Cloning and Base Sequencing of Full-Length cDNA Clone Encoding Tumor Antigen Protein KE-4-derived cDNA Library described in the above (3) of Reference Example was plated on LB agar medium containing ampicillin (50 µg/ml). The colonies thus obtained were then transferred and fixed on Hybond-N+ nylon membrane (Amersham) according to the manufacturer's protocol. The same 6DI probe as that used in (5) of Reference Example was employed for hybridization and autoradiography under the same conditions as those used in (5) of Reference Example, in order to select colonies which contain recombinant plasmids having the cDNA for tumor antigen protein gene incorporated. Furthermore, recombinant plasmids were recovered from the colonies selected, treated with restriction enzymes Not I and Sal I, and then electrophoresed on agarose to determine the length of incorporated cDNAs. A recombinant plasmid incorporating cDNA of about 2.5 kb was selected, and named K3. The base sequence of the cDNA region in this plasmid K3 was determined using DyeDeoxy Terminator Cycle Sequencing kit (Perkin-Elmer). The base sequence thus determined is shown in SEQ ID NO: 1. The full-length of the cDNA was 2527 base pairs. The amino acid sequence (800 amino acids) encoded by the base sequence of SEQ ID NO: 1 is shown in SEQ ID NO: 2.

The analysis indicated that the base sequence shown in SEQ ID NO: 1 does not share sequence homology with known tumor antigen protein genes derived from melanomas and proved to be a different gene. The search for the base sequence of SEQ ID NO: 1 using WWW Entrez database revealed that part of the base sequence exhibits high homology of more than 90% to three gene sequences, functions thereof are unknown, decoded by WashU-Merck EST Project and registered at GENBANK under Accession Nos. R89163, R62890, and R00027. R89163, R62890 and R00027 correspond to the sequences at positions 1893–2267; 2018–2389; and 2024–2510, respectively of SEQ ID NO: 1. These three sequences, however, are those located at 3' to the initiation codon in the base sequence shown in SEQ ID NO: 1, and therefore, the corresponding amino acid sequences cannot be determined.

After determination of the base sequence as described above, the plasmid K3 was introduced into *E. coli* JM109 to obtain *E. coli* JM109(K3) which is a transformant for storage containing the novel tumor antigen protein cDNA. *E. coli* JM109(K3) has been deposited at The National Institute of Bioscience and Human Technology (1-1-3 Higashi, Tsukuba, Ibaraki, Japan) under International Deposition No. FERM BP-5951 on May 22, 1997.

Furthermore, cDNA library (GIBCO BRL, Inc.) derived from normal human tissue (peripheral blood lymphocyte) was also screened in the manner as described above. The screening resulted in cloning of a recombinant plasmid into which cDNA of about 2.5 kb has been incorporated. When the base sequence was determined, the said cDNA thus cloned was identical with that shown in SEQ ID NO: 1 except for the base at 812 (position 812 for normal human tissue was T). This indicates that in connection with the full-length gene comprising the gene encoding the tumor antigen protein shown in SEQ ID NO: 1, almost the same genes are expressed in both cancer cells and normal human tissue.

VA-13 Cells were then doubly transfected with the recombinant plasmid K3 containing cDNA for the novel tumor antigen protein gene and another recombinant plasmid containing cDNA for HLA-A2601, and used as target cells as described in the above (4). The amount of IFN-γ produced by the reaction of KE-4CTL was determined according to the method as described in the above (4). The results are shown in the following TABLE 2.

TABLE 2

| Target cell | Amount of IFN-γ produced by KE-4CTL[1)] (pg/ml) |
|---|---|
| VA-13 cell + HLA-A2601 + K3 | 1439 |
| VA-13 cell + HLA-A0201[2)] + K3 | 10 |

[1)]Values obtained by subtracting the amount (background) of IFN-γ produced by KE-4CTL in response to VA-13 cells transfected with each HLA.
[2)]For comparison, HLA of different type was transfected.

(These date was obtained by transfection of the following amounts of DNA: 200 ng of HLA-A2601 or HLA-A0201, 100 ng of K3.)

Based on the above results, it was confirmed that the obtained cDNA encoded a tumor antigen protein.

(7) Identification of Tumor Antigen Peptide

From the recombinant plasmid 6DI cloned in the above (4) into which partial cDNA of the novel tumor antigen protein gene have been incorporated, plasmids containing partial cDNA of various length prepared through the deletion from tumor antigen protein gene using Deletion Kit for Kilo-Sequence (Takara Shuzo Co.) according to the manufacturer's protocol were obtained. These plasmids were introduced into *E. coli* ElectroMax DH10B/p3™ cells (Gibco BRL). The cells were plated on agar medium, and 50 colonies were selected at random. From the colonies, plasmid DNAs were prepared, subjected to electrophoresis, and 5 clones which contained plasmids having appropriate length selected.

According to the method described in the above (4), VA-13 cells were doubly transfected with HLA-A2601 cDNA and the above plasmid DNA, cocultured with KE-4CTL, and IFN-γ in the culture medium was quantitatively determined according to the method described in (4). As a result, it was found that the transfectant with a plasmid lacking the base sequence after position 2253 in SEQ ID NO: 1 had no IFN-γ-inducing activity on KE-4CTL. It was therefore suggested that peptides having the sequence after about position 739 in the amino acid sequence of SEQ ID NO: 2 may have IFN-γ-inducing activity on KE-4CTL.

Thus, a series of 21 different peptides each consisting of successive 10 amino acid residues in the amino acid sequence after position 730 in SEQ ID NO: 2 were synthesized so that they each have the amino acid sequence shifted serially by three amino acid residues. Using these peptides, IFN-γ in culture medium was determined as described above except that the antigen presentation was achieved by pulsing HLA-A2601 cDNA-transfected VA-13 cells with the peptides. As the result, IFN-γ-inducing activity was observed in the peptides having the amino acid sequences of positions 736 to 745 (736–745), positions 748 to 757 (748–757), and positions 784 to 793 (784–793) in SEQ ID NO: 2.

For each of these three peptides, additional peptides consisting of 9 amino acid residues were synthesized by truncating the N- or C-terminal residue, and used for measurement of IFN-γ-inducing activity in a similar manner. Stronger IFN-γ-inducing activity was observed for the peptides having the amino acid sequences of positions 736 to 744 (736–744), positions 749 to 757 (749–757), and positions 785 to 793 (785–793) in SEQ ID NO: 2. The results are shown in TABLE 3.

TABLE 3

| Pulsed cell | Peptide | Amount of INF-γ produced by KE4-CTL cells (pg/ml) |
|---|---|---|
| VA-13/A2601[1] | "736–744" | 203 |
| VA-13/A0201[2] | "736–744" | 44 |
| VA-13/A2601 | "749–757" | 183 |
| VA-13/A0201 | "749–757" | 89 |
| VA-13/A2601 | "785–793" | 394 |
| VA-13/A0201 | "785–793" | 102 |

[1]VA-13 cells transfected with HLA-A2601 cDNA
[2]VA-13 cells transfected with different HLA-A0201 cDNA as a control The results in TABLE 3 indicate that these peptides function as HLA-A26-restricted tumor antigen peptides.

HLA-A24-restricted tumor antigen peptides were then identified as follows.

There are certain rules (motifs) in the sequences of antigen peptides bound and presented by HLA molecules. Concerning the motif for HLA-A24, it is known that in the sequence of peptides consisting of 8 to 11 amino acids, the amino acid at the second position from the N-terminus is phenylalanine, tyrosine, methionine, or tryptophan, and the amino acid at the C-terminus is phenylalanine, leucine, isoleucine, tryptophan, or methionine (*Immunogenetics*, 41:178–228, 1995; *J. Immunol.*, 152: 3913, 1994; *J. Immunol.*, 155:4307, 1994).

Thus, another peptide consisting of the segment from position 690 to position 698 (690–698; SEQ ID NO: 3) in SEQ ID NO: 2 which corresponds to the above motif was further synthesized. VA-13 cells transfected with HLA-2402 cDNA was then pulsed with said peptide, and IFN-γ-inducing activity on KE-4CTL was measured as described above. The results are shown in TABLE 4.

TABLE 4

| Pulsed cell | Peptide | Amount of INF-γ produced by KE4-CTL cells (pg/ml) |
|---|---|---|
| VA-13 | "690–698" | 157 |
| VA-13/A2402[1] | "690–698" | 269 |
| VA-13/A0201[2] | "690–698" | 166 |

[1]VA-13 cells transfected with HLA-A2402 cDNA
[2]VA-13 cells transfected with different HLA-A0201 cDNA as a control The results in TABLE 4 suggest that the peptide "690–698 (SEQ ID NO: 3)" functions as a tumor antigen peptide.

(8) Induction of CTL from Peripheral Blood Lymphocytes by Tumor Antigen Peptides The inventors have investigated whether antigen-specific CTL can be induced from peripheral blood lymphocytes of the cancer patient from whom KE-4 was derived, by in vitro stimulation with the tumor antigen peptides described in the above (7). Tumor antigen peptides used were those having the sequences of "736–744", "749–757", and "690–698", obtained above in (7) of Reference Example. Frozen peripheral blood lymphocytes, which had been separated from the above cancer patient using Ficoll method, were awoke, transferred to 24-well plate at about $2 \times 10^6$ cells/well, and cultured in RPMI 1640 medium containing 10% FCS and IL-2 (100 U/ml). To stimulate the peripheral blood lymphocytes, the above tumor antigen peptide was added to the culture medium at 10 μg/ml. One week later, 10 μg/ml of the above tumor antigen peptide was added together with about $1 \times 10^5$ cells of X ray-radiated (50 Gy) peripheral blood lymphocytes for the second stimulation. After additional one week, the third stimulation was conducted in a similar manner.

As for peptides having the sequences of "736–744" and "749–757", peripheral blood lymphocytes were recovered one week after the third stimulation, and measured for their cytotoxic activity (specific lysis) using, as target cells, $^{51}$Cr-labeled KE-4 and another esophageal cancer cell line KE-3 of which HLA-A loci are A2402 and A2, according to the method described in D. D. Kharkevitch et at., *Int. J. Cancer*, 58:317 (1994). The results are shown in TABLE 5.

TABLE 5

| Effector cell | Target cell | Specific lysis (%) |
|---|---|---|
| Peripheral blood lymphocytes stimulated with "736–744" | KE-4 | 22.1 |
| | KE-3 | 3.7 |
| Peripheral blood lymphocytes stimulated with "749–757" | KE-4 | 35.9 |
| | KE-3 | 24.2 |

When stimulated with the peptide having the sequence of "736–744", KE-4 was severely injured, whereas the negative control KE-3 was not injured. It was therefore demonstrated that CTL specific for KE-4 was induced. Similarly, when stimulated with the peptide having the sequence of "749–757", stronger cytotoxic activity was observed on KE-4, although nonspecific cytotoxic activity was also observed on KE-3, indicating that CTL specific for KE-4 was induced.

For peptide having the sequence of "690–698 (SEQ ID NO: 3)", peripheral blood lymphocytes were recovered after the third stimulation, and further cultured in RPMI-1640 medium containing 10% FCS, 50% AIM-V (Gibco BRL), and IL-2 (100 U/ml). Then, the cytotoxic activity was measured as above using $^{51}$Cr-labeled KE-4 and VA-13 cells as target cells. In addition, lymphocytes were isolated from peripheral blood of a normal individual of which HLA-A loci were homozygous A24, and measured for their cytotoxic activity (specific lysis) in the same manner as above using, as target cells, $^{51}$Cr-labeled KE-4 and lung cancer cell line QG-56 of which HLA-A loci are homozygous A2601. The results are shown in TABLE 6.

TABLE 6

| Effector cell | Target cell | Specific lysis (%) |
| --- | --- | --- |
| "690–698" - Stimulated peripheral blood lymphocytes from a cancer patient | KE-4 | 24.7 |
| | VA-13 | 13.8 |
| "690–698" - Stimulated peripheral blood lymphocytes from a normal individual | KE-4 | 17.7 |
| | QG-56 | 11.5 |

When peripheral blood lymphocytes from a cancer patient and from a normal individual were stimulated with the peptide having the sequence of "690–698 (SEQ ID NO: 3)", stronger cytotoxic activity was observed on KE-4, although nonspecific cytotoxic activity was also observed on the negative controls VA-13 and QG-56 cells. The above results indicate that CTLs specific for KE-4 were induced.

EXAMPLE 1

Synthesis of Tumor Antigen Peptide Derivatives

As described above, there are certain rules (motifs) in the sequences of antigen peptides bound and presented by HLA molecules. Concerning the motif for HLA-A24, it is known that in the sequence of peptides consisting of 8 to 11 amino acids, the amino acid at the second position from the N-terminus is phenylalanine, tyrosine, methionine, or tryptophan, and the amino acid at the C-terminus is phenylalanine, leucine, isoleucine, tryptophan, or methionine (*Immunogenetics*, 41:178–228, 1995; *J. Immunol.*, 152: 3913, 1994; *J. Immunol.*, 155:4307, 1994). With regard to the peptide "690–698 (SEQ ID NO: 3)" which was identified as an HLA-A24-restricted tumor antigen peptide in the foregoing (7) and (8) of Reference Example, amino acid sequences of peptide derivatives containing amino acid substitution(s) according to the above motif are shown in SEQ ID NO: 4.

A variety of such tumor antigen peptide derivatives were prepared in which the second and/or ninth amino acid residue(s) of the HLA-A24-restricted tumor antigen peptide consisting of the amino acid sequence shown in SEQ ID NO: 3 were altered on the basis of the above-mentioned rules.

The following are several specific examples:
a) Glu-Tyr-Arg-Gly-Phe-Thr-Gln-Asp-Trp (SEQ ID NO: 7),
b) Glu-Tyr-Arg-Gly-Phe-Thr-Gln-Asp-Leu (SEQ ID NO: 6),
c) Glu-Tyr-Arg-Gly-Phe-Thr-Gln-Asp-Ile (SEQ ID NO: 5),
d) Glu-Phe-Arg-Gly-Phe-Thr-Gln-Asp-Phe (SEQ ID NO: 8),
e) Glu-Phe-Arg-Gly-Phe-Thr-Gln-Asp-Trp (SEQ ID NO: 9), These peptides were synthesized by the Fmoc method using Advanced Chemtech MPS 350, and then purified by HPLC using YMC-Pack ODS-A SH-363-5 column. The purified products were all at or greater than 95% purity.

The method of synthesizing peptide derivatives are described below in more detail in reference to the exemplary peptides:
(1) Glu-Tyr-Arg-Gly-Phe-Thr-Gln-Asp-Ile (SEQ ID NO: 5);
(2) Glu-Tyr-Arg-Gly-Phe-Thr-Gln-Asp-Leu (SEQ ID NO: 6); and
(3) Glu-Tyr-Arg-Gly-Phe-Thr-Gln-Asp-Trp (SEQ ID NO: 7).

(1) Synthesis of Glu-TyrArg-Gly-Phe-Thr-Gln-Asp-Ile (SEQ ID NO: 5)

Fmoc-Ile-Alko Resin (0.62 mmol/g, 100–200 mesh) was used as the resin. Using 100 mg of this resin, the synthesis was started according to Schedule 1 described below in TABLE 7 to couple the following residues in order: Fmoc-Asp(OtBu), Fmoc-Gln-OH, Fmoc-Thr(tBu)-OH, Fmoc-Phe-OH, Fmoc-Gly-OH, Fmoc-Arg(Pmc)-OH, Fmoc-Tyr(tBu)-OH, and Fmoc-Glu(OtBu)-OH. After the completion of coupling, the procedures were carried out up to Step 3 of Schedule 1 to obtain the peptide resin.

To this peptide resin, 2 ml of Reagent K (5% phenol, 5% thioanisole, 5% $H_2O$, and 2.5% ethanedithiol in TFA) was added and allowed to react for 2.5 hours at room temperature. To the resin was added 10 ml of diethyl ether under cooling with ice, and the mixture was stirred for 10 minutes, filtered, and then washed with 10 ml of diethyl ether. To the filter cake, 10 ml of aqueous acetic acid was added and the mixture was stirred for 30 minutes. The resin was then filtered off, and washed with 4 ml of aqueous acetic acid. After lyophilizing the filtrate and washing, the resultant crude peptide was dissolved in aqueous acetic acid, and loaded onto a reverse phase packing material YMC-Pack ODS-A SH-363-5 column (30 φ×250 mm) pre-equilibrated with 0.1% aqueous TFA. The column was washed with 0.1% aqueous TFA, and eluted while increasing the concentration of acetonitrile up to 24% over 200 minutes at a flow rate of 7 ml/min. The eluate was monitored at A 220 nm. The fractions containing the desired product were combined together and lyophilized to obtain 47.8 mg of Glu-Tyr-Arg-Gly-Phe-Thr-Gln-Asp-Ile (SEQ ID NO: 5).

The resultant peptide Glu-Tyr-Arg-Gly-Phe-Thr-Gln-Asp-Ile (SEQ ID NO: 5) had a retention time of 19.3 minutes when analyzed by a reverse phase packing material YMC-PACK ODS-AM AM-303 column (4.6 φ×250 mm) eluting with 0 to 60% linear gradient of acetonitrile containing 0.1% TFA. The amino acid analysis and mass spectrometry of the said peptide were consistent with the theoretical values.

Amino Acid Analysis

Hydrolysis: 1% phenol/6N aqueous hydrochloric acid, 110° C., 24 hours; Analytical method: the ninhydrin method; *: reference amino acid; theoretical values are indicated in parentheses.

Asx: 0.94 (1)
Thr: 0.91 (1)
Glx: 1.94 (2)
Gly: 0.99 (1)
*Ile: 1.00 (1)
Tyr: 0.93 (1)
Phe: 0.98 (1)
Arg: 0.95 (1)

Mass spectrum (FAB): [M+H]+: 1128

TABLE 7

Schedule 1

| Step | | (min) x times* |
|---|---|---|
| 1. washing | DMF 1.2 ml | 1 × 2 |
| 2. deprotection | 50% piperidine/DMF | 12 × 1 |
| 3. washing | DMF 1.2 ml | 1 × 7 |
| 4. coupling | an amino-protected amino acid (5 eq.)/ NMP solution 0.9 ml, DIC. (5 eq.)/NMP solution 0.3 ml | 30 × 1 |
| 5. washing | DMF 1.2 ml | 1 × 2 |
| 6. coupling | an amino-protected amino acid (5 eq.)/ NMP solution 0.9 ml, DIC (5 eq.)/NMP solution 0.3 ml | 30 × 1 |
| 7. washing | DMF 1.2 ml | 1 × 4 |

*Duration (min) × the number of times of treatment (2) Synthesis of Glu-Tyr-Arg-Gly-Phe-Thr-Gln-Asp-Leu (SEQ ID NO: 6)

In the same manner as that of the foregoing section (1), using 100 mg of Fmoc-Leu-Alko Resin (0.54 mmol/g, 100–200 mesh), Fmoc-Asp (OtBu)-OH, Fmoc-Gln-OH, Fmoc-Thr(tBu)-OH, Fmoc-Phe-OH, Fmoc-Gly-OH, Fmoc-Arg(Pmc)-OH, Fmoc-Tyr(tBu)-OH, and Fmoc-Glu(OtBu)-OH were coupled in order, and the product was then deprotected. The resultant crude peptide was dissolved in aqueous acetic acid and loaded onto a reverse phase packing material YMC-Pack ODS-A SH-363-5 column (30 φ×250 mm) pre-equilibrated with 0.1% aqueous TFA. The column was washed with 0.1% aqueous TFA, and eluted while increasing the concentration of acetonitrile up to 25% over 200 minutes at a flow rate of 7 ml/min. The eluate was monitored at A 220 nm. The fractions containing the desired product were combined and lyophilized to obtain 52.5 mg of Glu-Tyr-Arg-Gly-Phe-Thr-Gln-Asp-Leu (SEQ ID NO: 6).

The resultant peptide Glu-Tyr-Arg-Gly-Phe-Thr-Gln-Asp-Leu (SEQ ID NO: 6) had a retention time of 19.6 minutes when analyzed by a reverse phase packing material YMC-PACK ODS-AM AM-303 column (4.6 φ×250 mm) eluting with 0 to 60% linear gradient of acetonitrile containing 0.1% TFA. The amino acid analysis and mass spectrometry of the said peptide were consistent with the theoretical values.

Amino Acid Analysis

Hydrolysis: 1% phenol/6N aqueous hydrochloric acid, 110° C., 24 hours; analytical method: the ninhydrin method; *: reference amino acid; theoretical values are indicated in parentheses.

Asx: 0.97 (1)
Thr: 0.94 (1)
Glx,; 1.98 (2)
Gly: 1.02 (1)
*Leu: 1.00 (1)
Tyr: 0.94 (1)
Phe: 1.00 (1)
Arg: 0.97 (1)
Mass spectrum (FAB): [M+H]+: 1128

(3) Synthesis of Glu-Tyr-Arg-Gly-Phe-Thr-Gln-Asp-Trp (SEQ ID NO: 7)

In the same manner as that of the foregoing section (1), using 100 mg of Fmoc-Trp(Boc)-Alko Resin (0.65 mmol/g, 100–200 mesh), Fmoc-Asp (OtBu)-OH, Fmoc-Gln-OH, Fmoc-Thr(tBu)-OH, Fmoc-Phe-OH, Fmoc-Gly-OH, Fmoc-Arg(Pmc)-OH, Fmoc-Tyr(tBu)-OH, and Fmoc-Glu(OtBu)-OH were coupled in order, and the product was then deprotected. The resultant crude peptide was dissolved in aqueous acetic acid and loaded onto a reverse phase packing material YMC-Pack ODS-A SH-363-5 column (30 φ×250 mm) pre-equilibrated with 0.1% aqueous TFA. The column was washed with 0.1% aqueous TFA, and eluted while increasing the concentration of acetonitrile up to 26% over 200 minutes at a flow rate of 7 ml/min. The eluate was monitored at A 220 nm. The fractions containing the desired product were combined and lyophilized to obtain 14.0 mg of Glu-Tyr-Arg-Gly-Phe-Thr-Gln-Asp-Trp (SEQ ID NO: 7).

The resultant peptide Glu-Tyr-Arg-Gly-Phe-Thr-Gln-Asp-Trp (SEQ ID NO: 7) had a retention time of 20.7 minutes when analyzed using a reverse phase packing material YMC-PACK ODS-AM AM-303 column (4.6 φ×250 mm) eluting with 0 to 60% linear gradient of acetonitrile containing 0.1% TFA. The amino acid analysis (Trp could not be detected) and mass spectrometry of the said peptide were consistent with the theoretical values.

Amino Acid Analysis

Hydrolysis: 1% phenol/6N aqueous hydrochloric acid, 110° C., 24 hours; analytical method: the ninhydrin method; *: reference amino acid; theoretical values are indicated in parentheses.

Asx: 0.67 (1)
Thr: 0.96 (1)
Glx: 2.00 (2)
Gly: 1.02 (1)
Tyr: 0.96 (1)
*Phe: 1.00 (1)
Arg: 1.01 (1)
Mass spectrum (FAB): [M+H]+: 1202

EXAMPLE 2

Activity Measurement of Tumor Antigen Peptide Derivatives

The peptides prepared in Example 1 can be examined for the IFN-γ-inducing activity as described in (7) of Reference Example or the CTL-inducing ability as described in (8) of Reference Example so as to demonstrate that these peptides have functions as a tumor antigen peptide. An example is shown below.

Figure 2:
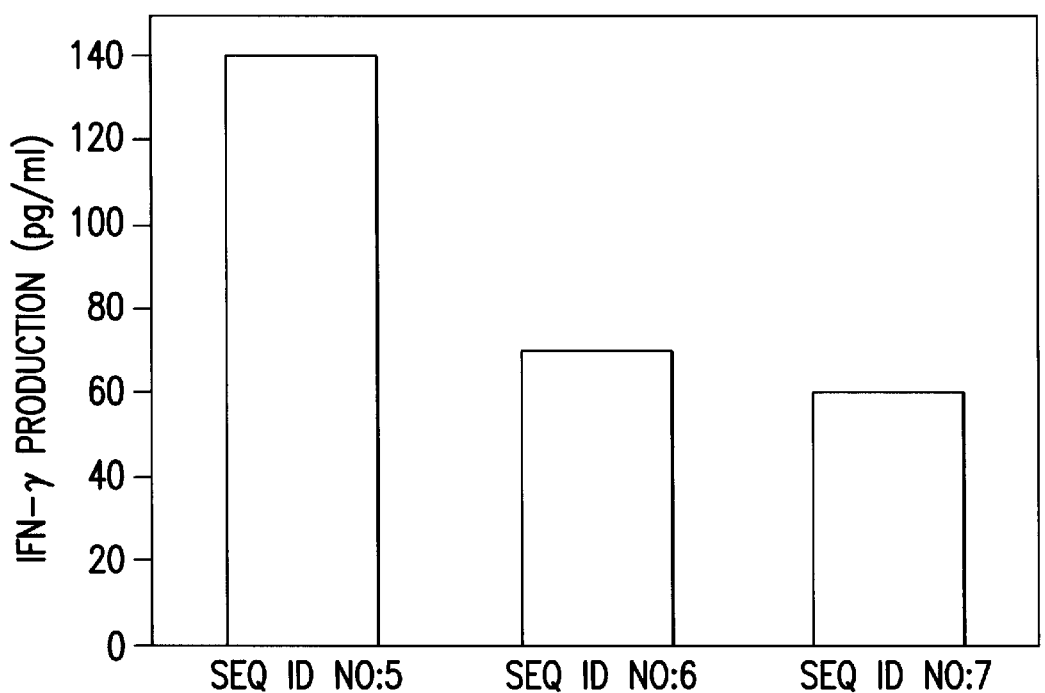
FIG. 2 depicts a bar graph showing the in vitro IFN-γ-inducing activities of peptides having the amino acid sequences shown in SEQ ID NOs: 5, 6, and 7. Specifically, peripheral blood lymphocytes from an HLA-A24-positive healthy individual were stimulated with the above peptide derivatives, and the amounts of IFN-γ produced by the stimulated lymphocytes were measured in the presence of HLA-A24-positive KE-4 cells expressing the tumor antigen. It can be seen from FIG. 2 that CTLs are induced by each peptide derivative of SEQ ID NOs: 5, 6, and 7.

Peripheral blood lymphocytes obtained from an HLA-A24-positive healthy human were subjected to in vitro peptide stimulation in the same manner as Reference Example (8) using the three tumor antigen peptide derivatives (SEQ ID NOs: 5–7) synthesized in the above Example 1 to examine whether or not the peptides can induce CTLs. The peripheral blood lymphocytes were recovered one week after the third stimulation with the peptides, and the amount of IFN-γ produced by the peripheral blood lymphocytes in response to the stimulation was measured using, as target cells, HLA-A24-positive KE-4 cells expressing the tumor antigen. Separately, the amount of IFN-γ produced by the peripheral blood lymphocytes in response to the stimulation was measured using, as target cells, HLA-A24-negative VA-13 cells in a similar and used as the background value. The antigen-specific CTL activity was calculated by subtracting the background amount of IFN-γ produced against VA-13 cells from the amount of IFN-γ produced against KE-4 cells. The results are shown in FIG. 2. It was demonstrated that CTLs were induced by each of the peptide derivatives shown in SEQ ID NOs: 5, 6, and 7. In particular, the tumor antigen peptide derivative shown in SEQ ID NO: 5 exhibited a strong activity of inducing IFN-γ production.

Alternatively, the same activity measurement as that described above may also be carried out using commercially available SKG-IIIa cells (JCR B0232) instead of KE-4 cells as tumor antigen- and HLA-A24-positive target cells.

Industrial Applicability

The novel tumor antigen peptide derivatives provided by the present invention are useful in prophylaxis, treatment, or diagnosis of a wide range of tumors.

Sequence Listing Free Text

In the amino acid sequence shown in SEQ ID NO: 4, the second amino acid is phenylalanine, tyrosine, methionine, or tryptophan, and the ninth amino acid is phenylalanine, leucine, isoleucine, tryptophan, or methionine.

What is claimed is:

1. A tumor antigen peptide derivative which comprises the amino acid sequence of SEQ ID No: 3, wherein the amino acid residue at the second and/or the ninth position of SEQ ID No: 3 are substitued with another amino acid residue, which derivative binds HLA-A24 such that the derivative is recognized by cytotoxic T cells.

2. A tumor antigen peptide derivative of claim 1 comprising SEQ ID NO: 4.

3. A tumor antigen peptide derivative of claim 2, wherein the amino acid at the ninth position of SEQ ID NO: 4 is substituted with tryptophan, leucine, or isoleucine.

4. A tumor antigen peptide derivative of claim 2, wherein the amino acid at the second position of SEQ ID NO: 4 is substituted with phenylalanine.

5. A tumor antigen peptide derivative of claim 2, wherein the amino acid at the ninth position of SEQ ID NO: 4 is substituted with tryptophan, leucine, or isoleucine, and the amino acid at the second position of SEQ ID NO: 4 is substituted with phenylalanine.

6. A tumor antigen peptide derivative of claim 3 comprising SEQ ID NO: 5.

7. A composition comprising at least one tumor antigen peptide derivative selected from those derivatives set forth in any one of claims 1–6.

* * * * *